(12) United States Patent
Ito et al.

(10) Patent No.: US 6,432,688 B1
(45) Date of Patent: Aug. 13, 2002

(54) AMINO ALCOHOL DEHYDROGENASE CONVERTS KETO ALCOHOL TO AMINO ALCOHOL AND AMINO ALCOHOL TO KETO ALCOHOL

(75) Inventors: Nobuya Ito, Kosugi-machi; Akinobu Matsuyama, Tsukuba; Yoshinori Kobayashi, Joetsu, all of (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/484,888

(22) Filed: Jan. 18, 2000

(30) Foreign Application Priority Data

Jan. 18, 1999 (JP) .......................................... 11-009679

(51) Int. Cl.[7] .......................... C12N 9/04; C12N 1/12; C12P 13/04; C12P 7/26; C12P 7/02
(52) U.S. Cl. ...................... 435/190; 435/106; 435/147; 435/148; 435/155; 435/252.1; 435/253.5; 435/252.34; 435/830; 435/874; 435/876; 435/886; 435/897
(58) Field of Search .................................. 435/190, 106, 435/147, 148, 155, 252.1, 253.5, 252.34, 886, 897, 830, 874, 876

(56) References Cited

U.S. PATENT DOCUMENTS

| | | | | |
|---|---|---|---|---|
| 4,138,292 A | * | 2/1979 | Chibata et al. ............. | 435/280 |
| 4,950,606 A | | 8/1990 | Stirling et al. ............. | 435/280 |
| 5,126,245 A | * | 6/1992 | Motoyama et al. ........... | 435/15 |
| 5,300,437 A | * | 4/1994 | Stirling et al. ............. | 435/280 |

FOREIGN PATENT DOCUMENTS

| EP | 0 857 790 A1 | 8/1998 |
|---|---|---|
| JP | 63-273486 | 11/1988 |

OTHER PUBLICATIONS

Yonaha et al., Journal of Biological Chemistry, vol. 260, No. 6, 3265–3268, 1985.*
Yonaha et al., European Jpurnal of Biochemistry, 146, 101–106, 1985.*
Adachi et al., "Characterization of Quinohemoprotein . . . ," Biosci, Biotechnol. Biochem., 62(3):469–478, 1998.
Nakamichi et al., "Asymmetric amination . . . ," Appl. Microbiol. Biotechnol 33:637–640, 1990.

* cited by examiner

Primary Examiner—David M. Naff
Assistant Examiner—Mike Meller
(74) Attorney, Agent, or Firm—Fish & Richardson P.C.

(57) ABSTRACT

A purified amino alcohol dehydrogenase which reductively converts a keto alcohol into an amino alcohol and oxidatively converts an amino alcohol into a keto alcohol is disclosed. The enzyme is NAD(H) dependent, has a molecular weight of 100,000 Da when determined by gel filtration, has a optimum temperature of about 30° C. in reductive amination, an optimum pH of 10.0 in an oxidative deamination and of 7.0 in a reductive amination and can be isolated from *Steptomyces virginiae*.

2 Claims, No Drawings

AMINO ALCOHOL DEHYDROGENASE CONVERTS KETO ALCOHOL TO AMINO ALCOHOL AND AMINO ALCOHOL TO KETO ALCOHOL

FIELD OF INVENTION

This invention relates to novel amino alcohol dehydrogenases, methods for preparing the enzymes, and uses of the enzymes.

BACKGROUND OF THE INVENTION

Amino acid dehydrogenases, amine dehydrogenases, aminotransferases have been known to convert a carbonyl group to an amino group. Amino acid dehydrogenase reductivel aminates keto acid to amino acid. Only keto acids and amino acids can be substrates for the enzyme (Experiments of Biochemistry, Vol. 11, ed. by Japan Society of Biochemistry, Amino acid metabolism and biological amine (I) 193–218, J. Org. Chem., 55, 5567, 1990; Fermentation and Industry 40, 301–311, 1982). The inventors examined substrate specificity of commercially available amino acid dehydrogenases, such as L-alanine dehydrogenase and L-glutamic acid dehydrogenase, and found that they do not have any enzymatic activity on other amino acid alcohols. In other words, these NAD (H)-dependent amino acid dehydrogenases only act on very limited amino acids. Amine alcohols include many useful compounds like synthetic intermediates for pharmaceuticals, such as serinol. Any enzyme that can be used for synthesizing these amino alcohols has not been reported.

Amine dehydrogenase uses tryptophane-tryptoquinone (TPQ) or TPQ and heme as prosthetic groups, and uses phenazinementasulfate (PMS), an artificial electron carrier, as an electron acceptor. It is independent of AND(H). This enzyme acts on substrates to produce aldehydes. The substrates include aliphatic 1-amine, such as methylamine, propylamine, n-butylamine, or 1,6-diaminohexane, and some of the enzymes act on arylamine such as 2-phenethylamine or tyramine (Biosci. Biotechnol. Biochem. 62: 469–478, 1998). It does not act, however, on amino alcohols, amino acids, and aliphatic 2-amines at all.

Aminotransferase transfers an amino group of an amino acid donor to keto acid, thereby converting the keto acid into amino acid. ω-Amino acid transaminase or the like, among others, are known to produce an amino compound from ketone, not keto acid (Unexamined Published Japanese Patent Application No. (JP-A) Hei 3-103192, WO97/15682, Appl. Microbiol. Biotechnol. 33, 634–640, 1990, Examined Published Japanese Patent Application No. (JP-B) Hei 4-11194).

No alcohol dehydrogenase which converts keto alcohol into amino alcohol has been reported. The enzymes which converts keto alcohol and keto acid into the corresponding amino alcohol and amino acid, those which converts keto alcohol, ketone, and aldehyde into the corresponding amino alcohol and amine, and those which converts keto alcohol, keto acid, ketone, and aldehyde into the corresponding amino alcohol, amino acid, and amine have not been reported. Furthermore, neither methods for producing such enzymes nor uses of the enzymes have been reported.

SUMMARY OF THE INVENTION

An objective of the present invention is to provide enzymes that can reversibly catalyze the redox reactions described below, production methods, and uses of the enzymes.

Reaction 1: Keto alcohol/amino alcohol

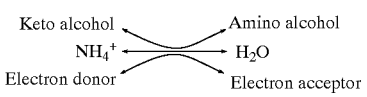

Reaction 2: Keto acid/amino acid

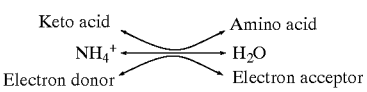

Reaction 3: Ketone or aldehyde/amine

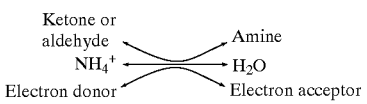

As a result of the investigation to achieve the above objective, the present inventors isolated microorganisms producing a novel dehydrogenase that converts keto alcohols into amino alcohols, the one that concerts keto alcohols and keto acids into the corresponding amino alcohols and amino acids, the one that converts keto alcohols, ketones, and aldehydes into the corresponding amino alcohols and amines, and the one that converts keto alcohols, keto acids, ketones, and aldehydes into the corresponding amino alcohols, amino acids, and amines. We purified the enzymes and named them amino alcohol dehydrogenases.

The present inventors also established a method for producing amino alcohol dehydrogenase, a method for producing amino alcohol from keto alcohol using the amino alcohol dehydrogenase, a method for producing amino acid from keto acid, and a method for producing amine from ketone or aldehyde.

Specifically, the present invention relates to an amino alcohol dehydrogenase described below, a method for producing it, and its uses.

(1) An amino alcohol dehydrogenase that reductively converts keto alcohol into amino alcohol, and oxidatively converts amino alcohol into keto alcohol, (2) The amino alcohol dehydrogenase of (1), which reductively converts keto acid into amino acid and oxidatively converts amino acid into keto acid, (3) The amino alcohol dehydrogenase of (1) or (2), which reductively converts ketone or aldehyde into amine and oxidatively converts amine into ketone or aldehyde.:, (4) The amino alcohol dehydrogenase of (1), (2) or (3), which is obtainable from a microorganism selected from the group consisting of the genera Streptomyces, Pseudomononas, Burkholdenia, and Arthrobacter, (5) The amino alcohol dehydrogenase of (4), wherein the microorganism belonging to the genus Streptomyces is selected from the group consisting of the species *Streptomyces virginiae, Streptomyces griseus, Streptomyces avidinii*, and *Streptomyces pseudovenezulae,*

(6) The amino alcohol dehydrogenase of (4), wherein the microorganism belonging to the genus Pseudomononas is,: the species *Pseudomonaonas fluorescens* or *Pseudomonas marginalis,*

(7) The amino alcohol dehydrogenase of (4), wherein the microorganism belonging to the genus Burkholdenia is the species *Burkholdenia cepacia,*

(8) The amino alcohol dehydrogenase of (4), wherein the microorganism belonging to the genus Arthrobacter is the species *Arthrobacter aurescens,*

(9) An amino alcohol dehydrogenase having the following physicochemical properties:
 (a) NAD(H)-dependent;
 (b) a molecular weight of a part of the subunit of about 46,000 Da when determined by SDS-polyacrylamide gel electrophoresis, and of the whole molecule of about 100,000 Da when determined by gel filtration;
 (c) substrate specificity, such that it acts on amino alcohols, amines, amino acids in the presence of $NAD^+$ to produce keto alcohols, ketones, aldehydes, and keto acids, and acts on keto alcohols, ketones, aldehydes, and keto acids in the presence of NADH and ammonium ions to produce amino alcohols, amines, and amino acids;
 (d) thermostability, such that it is relatively stable at 30° C. and inactivated at 40° C. or higher when heated at pH 7.0 for 30 min;
 (e) optimum temperature of about 30° C. in reductive amination at pH 7.0;
 (f) optimum pH of 10.0 in oxidative deamination and of 7.0 in reductive amination; and
 (g) stability, such that its activity is stable in the presence of glycerol or serinol, or phenylmethylsulfonylfluoride, a protease inhibitor,
(10) A method for producing amino alcohol dehydrogenase, the method comprising culturing a microorganism, which produces the amino alcohol dehydrogenase of any one of (1) to (9), and recovering the enzyme from the culture,
(11) A method for producing amino alcohol, the method comprising reacting keto alcohol with the amino alcohol dehydrogenase of any one of (1) to (9) in a reaction system, and recovering the corresponding amino alcohol from the reaction system,
(12) A method for producing amino acid, the method comprising reacting keto acid with the amino alcohol dehydrogenase of any one of (2) to (9) in a reaction system, and recovering the corresponding amino acid from the reaction system,
(13) A method for producing amine, the method comprising reacting ketone and aldehyde with the amino alcohol dehydrogenase of any one of (3) to (9) in a reaction system, and recovering the corresponding amine from the reaction system,
(14) A microorganism producing amino alcohol dehydrogenase of (1), which has the characteristics of the microorganism selected from the group consisting of *Arthrobacter aurescens* B151 identified by a deposit number of FERM P-17137, *Burkholdenia cepacia* B033 identified by a deposit number of FERM P-17138, *Pseudomonas fluorescens* B101 identified by a deposit number of FERMP-17139, *Pseudomonas marginalis* B102 identified by a deposit number of FERMP-17140, *Streptomyces griseus* TPC33081 identified by a deposit number of FERM P-17141, *Streptomyces avidinii* A044 identified by a deposit number of FERM P-17142, and *Streptomyces pseudovenezulae* A161 identified by a deposit number of FERM P-17143.

The present invention also provides a method for producing keto alcohol, keto acid, ketone, or aldehyde comprising reacting amino alcohol, amino acid, or amine with the amino alcohol dehydrogenase described above. In this method as well as the above methods (11) to (13), the microorganism of (14) or its treated product can be used in place of the amino alcohol dehydrogenase.

DETAILED DESCRIPTION OF THE INVENTION

Keto alcohol of the present invention can be represented by formula (1):

wherein R1 and R2 each represents an aliphatic hydrocarbon group, an alicyclic hydrocarbon group, an aryl group, or a heterocyclic group, where these groups are substituted with a hydroxyl group.

Amino alcohol can be represented by formula (2):

wherein R1 and R2 are as defined in formula (1).

Keto acid can be represented by formula (3):.

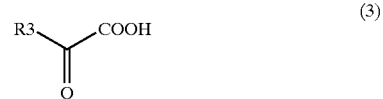

wherein R3 represents an aliphatic hydrocarbon group, an alicyclic hydrocarbon group, an aryl group or a heterocyclic group.

Amino acid can be represented by formula (4):

wherein R3 is as defined in formula (3).

Ketone or aldehyde can be represented by formula (5):

wherein R4 and R5 each represents a hydrogen atom, an aliphatic hydrocarbon group, an alicyclic hydrocarbon group, an aromatic hydrocarbon group, or a heterocyclic group, provided that R4 and R5 are not hydrogen atoms at the same time.

Amine can be represented by formula (6):

wherein R4 and R5 are as defined in formula (5).

An aliphatic hydrocarbon group used herein includes saturated or unsaturated aliphatic hydrocarbon groups. Examples are a straight or branched alkyl group having 1 to 12 carbon atoms, such as a methyl group, an ethyl group, a propyl group, an isopropyl group, a butyl group, an isobutyl group, an s-butyl group, a t-butyl group, a pentyl group, a hexyl group, an octyl group, a decyl group, etc.; an alkenyl group having; 1 to 12 carbon atoms, such as a vinyl group, an allyl group, a 1-propenyl group, an isopropenyl group, a 2-butenyl group, etc.; and an alkynyl group having 1 to 12 carbon atoms, such as a 2-propynyl group, a 2-butynyl group, etc. An alkyl group having 1 to 5 carbon atoms is preferable.

An alicyclic hydrocarbon group includes saturated or unsaturated alicyclic hydrocarbon groups. Examples are a cycloalkyl group having 3 to 10 carbon atoms, such as a cyclobutyl group, a cyclopentyl group, a cyclohexyl group, a cyclooctyl group etc.; and a cycloalkenyl group having 3 to 10 carbon atoms, such as a cyclopentenyl group, a cyclohexenyl group, etc.

An aryl group is, for example, those with: 6 to 14 carbon atoms, such as a phenyl group, a naphthyl group, etc.

A heterocyclic group includes the one containing at least one hetero atom selected from a nitrogen atom, an oxygen atom, and a sulfur atom. A heterocyclic group may be an aromatic heterocyclic group, a non-aromatic heterocyclic group, or a compound heterocyclic group.

A heterocyclic ring of the above-mentioned heterocyclic group includes a nitrogen-containing heterocyclic ring such as pyrroline, pyrrole, piperidine, piperazine, pyridine, pyrimidine, pyridazine, triazole, quinoline, etc.; an oxygen-containing heterocyclic ring such as tetrahydrofuran, furan, pyran, etc.; a sulfur-containing heterocyclic ring such as tetrahydrothiophene, thiophene, etc.; and a heterocyclic ring containing at least two hetero atoms selected from a nitrogen atom, an oxygen atom, and a sulfur atom, such as thiazoline, thiazolidine, thiazole, thiazine, morpholine, etc.

These groups may have substituents, including a halogen atom, a hydroxyl group, an alkyl group (for example, a $C_{1-5}$ alkyl group such as a methyl group, an ethyl group, a propyl group, an isopropyl group, etc.), an aryl group (for example, a $C_{6-14}$aryl group such as a phenyl group, a tolyl group, a chlorophenyl group, a naphthyl group, etc.), an oxo group, an alkoxy group (for example, a $C_{1-5}$ alkoxy group such as a methoxy group, an ethoxy group, etc.), an aryloxy group (for example, a phenoxy group, etc.), a mercapto group, analkylthio group (for example, a $C_{1-5}$alkylthio group such as a methylthio group, an ethylthio group, etc.), an arylthio group (for example, a $C_{6-14}$ arylthio group such as a phenylthio group, etc.), a carboxyl group, an ester group (for example, a $C_{1-6}$ alkoxycarbonyl group such as a methoxycarbonyl group, etc.; a $C_{2-12}$ acyloxy group such as an acetoxy group, etc.), an acyl group (for example, a $C_{2-12}$ acyl group such as an acethyl group, a benzoyl group, etc.), an amino group, a mono- or di-substituted amino group (for example, a mono- or di-$C_{1-5}$ alkylamino group such as a methylamino group, a dimethylamino group, etc.), a nitro group, etc. The number of substituents is, for example, 1 to 4.

A preferable keto alcohol in this invention is, for example, hydroxyacetone, dihydroxyacetone, 2-hydroxyacetophenone, 4-hydroxy-2-butanone, 5-hydroxy-4-octanone, etc. A preferable keto acid is, for example, pyruvic acid, oxalacetic acid, 2-oxoglutaric acid, etc. A preferable ketone or aldehyde is, for example, acetone, 2-butanone, 2-pentanone, 2-hexanone, acetophenone, 4-phenyl-2-butanone, n-butylaldehyde, n-hexylaldehyde, benzaldehyde, etc.

Microorganisms producing amino alcohol dehydrogenase can be isolated in the following procedures. Microorganisms isolated from the nature, or microorganisms available from depositary institutes are cultured by a standard method. If necessary, a compound that induces the enzyme, such as a substrate, or a compound that enhances the production of the enzyme, such as metal salts, etc. can be added to the culture medium. Microbial cells are harvested from the cultured broth, washed with, for example, buffer, if necessary, disrupted by a mechanical method using alumina, Dyno mill, etc. or treatment with an organic solvent, such as acetone, etc., to extract the present enzyme. The solid matters are removed from the extract by filtration or centrifugation to obtain a crude enzyme solution. This solution is added to tris-HCl buffer (pH 8.0–9.0) containing 0.5 mg/ml 2-(4-iodophenyl)-3-(4-nitrophenyl)-5-phenyl-2Htetrazolium chloride (INT), 10 mM serinol, and 1 mM $NAD^+$, and the mixture is incubated at 25° C. INT is reduced to red-purple formazan when $NAD^+$is reduced to NADH. Activity of amino alcohol dehydrogenase can be qualitatively or quantitatively measured by this color change.

A culture medium for the microorganism of this invention contains a carbon source such as glucose, glycerol, etc., which is known to be metabolized by microorganisms, a nitrogen source such as ammonium sulfate, ammonium nitrate, etc., inorganic nutrients or metals such as magnesium sulfate, iron (II) chloride, cobalt chloride etc. A natural organic nitrogen source such as yeast extract, meat extract, etc., can be added to the medium. Carbon sources adequate for each microorganism can be applied as an inducer.

Culture conditions are not particularly limited as long as microorganisms can grow. Preferable conditions are, for example, a pH range of 5 to 10 and a temperature range of 5 to 40° C. High yield can be obtained by culturing the microorganisms under aerobic conditions at a pH range of 6 to 8, a temperature of 20 to 40° C., for 12 hours to 5 days until achieving the maximum activity.

The enzymatic reaction can be performed by contacting a substrate with microbial cells which are harvested from a liquid medium or a plate medium by a known method. If desired, cells are treated with surfactants or organic solvents such as toluene to modify cell membrane permeability. The cells can also be immobilized on a supporting materials such as carageenan gel, alginate gel, polyacrylamide gel, cellulose, agar,.etc. using a known method. The crude enzymes which are partically purified by the method described below can also be used. These are included in the treated products of the microorganisms used herein. The microbial cells or their treated products are reacted in a two-phase system containing a substrate dissolved in an appropriate solvent such as n-hexane, ethyl acetate, etc. and buffer, etc. Alternatively, a substrate is dissolved in an aqueous organic solvent such as ethanol, dimethylformamide, etc., and mixed with a suspension of the microbial cells, their treated products, or the enzyme.

Amino alcohol dehydrogenase can be collected from a culture medium by separating microbial cells and a culture supernatant by centrifugation or another method. When the enzyme is intracellularly produced, the microbial cells are disrupted by, for example, lytic enzyme treatment, ultra-sonication, French press treatment, Dyno mill treatment, etc., to solubilize the enzyme. These treatments are used alone or in combination.

The solubilized enzyme can be purified by an appropriate combination of methods well known in the art. These methods include salting-out method with, for example, ammonium sulfate, anion exchange chromatography using, for: example, diethylaminoethylcellulose, cation exchange chromatography using, for example, carboxymethylcellulose, gel filtration using, for example, dextran gel, hydrophobic chromatography using a hydrophobic resin, and affinity chromatography, etc. An amino alcohol dehydrogenase preparation with desired purity can thus be obtained.

When the enzyme is extracellularly produced, culture supernatant is collected by a suitable separation method such as centrifugation and purified as described above to obtain an amino alcohol dehydrogenase fraction.

The amino alcohol dehydrogenase of the present invention can be obtained from the culture of microorganisms belonging to, for example, the genera Streptomyces, Pseudomonas, Burkholdenia, or Arthrobacter.

More specifically, ability to produce amino alcohols was confirmed in *Streptomyces virginiae* IFO 12827 and *Streptomyces ariseus* TPC 33081. IFO 12827 is recited in List of Cultures 10th ed. published by Institute of Fermentation, Osaka (IFO) and is available from IFO.

The present inventors identified the following microorganisms and confirmed their ability to produce amino alcohols. These newly isolated microorganisms have been deposited with National Institute of Bioscience and Human Technology, Agency of Industrial Science and Technology, Ministry of International Trading and Industry of 1-3, Higashi 1-Chome, Tsukuba, Ibaraki 305-0046 Japan) since Jan. 12, 1999.

*Arthrobacter aurescens* B151, Trust No. FERM BP-6995;
*Burkholdenia cepacia* B033, deposit No. FERM BP-6996;
*Pseudomonas fluorescens* B101, deposit No. FERMP BP-6997;
*Psedomonas marginalis* B102, deposit No. FERM P-17140;
*Streptomyces griseus* TPC 33081, deposit No. FERM P-17141;
*Streptomyces avidinii* A044, deposit No. FERM P-17142; and
*Streptomyces preudovenezulae* A161, deposit No. FERM P-17143.

The present invention provides a method for producing amino alcohols, amino acids, or amines using the above-mentioned amino alcohol dehydrogenase. Substrates for the enzymatic reaction is keto alcohols, keto acids, ketones, or aldehydes, which provides a basic structure of a product compound having amino group(s). The substrate is contacted with the amino alcohol dehydrogenase of the invention in the presence of ammonium ion as an additional substrate and an electron donor (a hydrogen donor) to perform reduction reaction, thereby producing the corresponding amino alcohols, amino acids, or amines (amination reaction). The following reaction formulae illustrate the methods for producing the above-mentioned compounds according to this invention.

Reaction 1: Keto alcohol/amino alcohol

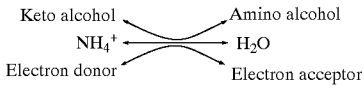

Reaction 2: Keto acid/amino acid

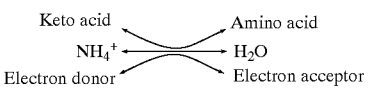

-continued
Reaction 3: Ketone or aldehyde/amine

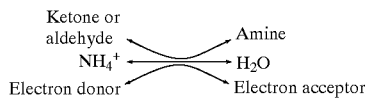

Compounds used as a substrate in this invention include various keto alcohols, keto acids, ketones, and aldehydes as described above. An ammonium ion ($NH_4^+$) that provides an amino group to the basic structure of the substrate is added to the reaction system in the form of an appropriate ammonium salt. The methods of the present invention for producing amino alcohols, amino aids, or amines can be carried out by contacting the amino alcohol dehydrogenase of this invention with an electron donor, NADH, as well as $NH_4^+$.

In the reductive amination reaction, 10 to 100 mM of a substrate (keto alcohol, keto acid, ketone, aldehyde), 200 to 300 mM of ammonium chloride, and 0.2 to 10 nM of NADH can be employed. These substrates and coenzymes are not necessarily completely dissolved in the reaction medium. The reaction temperature should be any temperature at which the reaction will proceed, and preferably 10 to 40° C. The pH during the reaction should be from 5 to 8, and preferably at 7. The reductive conditions can be achieved within the above-mentioned pH range.

In the oxidative deamination, 10 to 100 mM of a substrate, amino alcohol, amino acid, or amine, and 0.2 to 10 mM of $NAD^+$ can be used. Any temperature at which the reaction proceeds can be applied, and a range of 10 to 40° C. is preferable. A reaction pH should be from 8 to 11, and preferably 10. The oxidative conditions can be achieved within the above-mentioned pH range.

In both reductive amination and oxidative deamination, these substrates and coenzymes are not necessarily completely dissolved in the reaction medium. The substrate can be added at once at the initiation of the reaction. Alternatively, it can be added successively or intermittently to the reaction system so that the substrate concentration becomes too high. The reaction can be allowed to proceed for about 5 min to about 100 hours. The products can be isolated by a known method including, for example, extraction, concentration, ion exchange, electric dialysis, crystallization, etc.

The contact of enzyme, substrate, and coenzyme can be achieved by the mixing these three in a solution. The reaction solution can be a sparingly water-soluble organic solvent such as ethyl acetate, butyl acetate, toluene, chloroform, n-hexane, etc., or the two-phase system of such an organic solvent and aqueous medium. The reaction of the present invention can be achieved by using immobilized enzymes, membrane reactors, etc.

In the enzyme reaction of the present invention, the reaction conditions become gradually acidic with the consumption of NADH. To keep reductive conditions, a regeneration system of NADH can be combined with the above-mentioned system. $NAD^+$ can be regenerated to NADH by utilizing $NAD^+$ reducing ability of microorganisms (glycolysis, C1 compound metabolic pathway of methylotroph, etc.). The $NAD^+$ reducing ability can be enhanced by adding glucose, ethanol, or formic acid to the reaction system. Alternatively, microorganisms capable of regenerating NADH from $NAD^+$ or their treated products can be added. Such microorganisms are, for example, those producing glucose dehydrogenase, formate dehydrogenase, alcohol dehydrogenase, amino acid dehydrogenase, organic acid dehydrogenase (such as malate dehydrogenase, etc.), or their treated products, partially purified or purified enzymes described above. Reactants necessary for NADH regeneration reaction can be added to the reaction system for producing alcohol of the present invention as they are, or as their treated products. The reactants can also be contacted with the reaction system through a membrane that enables exchanging NADH.

The compound to be added to the reaction system for regenerating NADH, include, for example, glucose in the case of using glucose dehydrogenase, formic acid in the case of using formate dehydrogenase, ethanol or isopropanol in the case of the using alcohol dehydrogenase, and can be added at a molar ratio to a substrate ketone of 1:20, and preferably in 1 to 5 times excess amount to a substrate ketone. The enzymes for regenerating NADH such as glucose dehydrogenase, formate dehydrogenase, or alcohol dehydrogenase can be added in 0.1 to 100 times, and preferably 0.5 to 20 times amount of the enzymatic activity compared with that of the amino alcohol dehydrogenase of the invention.

Similarly, the reaction system for regenerating NADH to $NAD^+$ can also be combined with the oxidative deamination of the present invention. $NAD^+$ can be regenerated, for example, using ability to oxidize NADH (NADH oxigenase, etc.) of microorganisms in the presence of oxygen.

Amino alcohol dehydrogenase of the present invention has various uses due to its wide range of substrate specificity. For example, it can be used for enzymatic synthesis of useful compounds such as serinol.

Known enzymes converting a carbonyl group to an amino group, including amino acid dehydrogenases, amine dehydrogenases, and aminotransferases can act on limited combinations of, keto acid/amino acid. The amino alcohol dehydrogenases of the present invention are useful enzymes for solving these problems.

The present invention is illustrated in detail below with reference to Examples, but not to be construed as being limited thereto. In the following Examples, "%" indicates "w/v%" if not particularly specified.

EXAMPLE 1

Isolation of Microorganisms Producing Amino Alcohol Dehydrogenase

A soil sample suspended in saline (0.1 mL) was inoculated onto a plate medium (pH 7.0) containing 0.2% (w/v) serinol, 0.3% $KH_2PO_4$, 0.1% NaCl, 0.05% $MgSO_4 \cdot 7H_2O$, 1.5% agar and cultured at 30° C. under the aerobic condition for 1 to 7 days. The grown colony was inoculated onto the plate medium containing 0.71% peptone, 0.3% yeast extract, 1.5% agar (pH 7.0) for single colony separation and stored at 4° C. in a slant containing 0.2% serinol, 0.3% $KH_2PO_4$, 0.1% NaCl, 0.05% $MgSO_4 \cdot 7H_2O$, 0.1% yeast extract, and 1.5% agar.

In order to confirm the productivity of amino alcohol dehydrogenase in these stored strains, a crude enzyme solution was obtained by the following procedures. In the case of actinomyces, 50 ml of a culture medium. (pH 7.3) containing 1.5% soluble starch, 0.8% soytone, 0.5% meat extract, 0.3% glucose, 0.2% $K_2HPO_4$, 0.3% NaCl, 0.03% $MgSO_4 \cdot 7H_2O$, 0.01% $CaCl_2 \cdot 2H_2O$, 0.1% TM solution was added to an Erlenmeyer flask and sterilized. TM solution contains 0.05 g of $H_3BO_3$, 0.01 g of $CUSO_4 \cdot 5H_2O$, 0.025 g of KI, 0.1 g $FeCl_3 \cdot 6H_2O$, 0.05 g $MnCl_2 \cdot 4H_2O$, 0.02 g of $Na_2MoO_4 \cdot 5H_2O$, 0.05 g of $ZnSO_4 \cdot 7H_2O$, 0.1 g of $CoCl_2 \cdot 6H_2O$, and 100 ml of distilled water. Each strain was inoculated to the sterilized medium and cultured at 30° C. for 48 hours. The microbial cells were then disrupted to obtain a crude enzyme solution.

In the case of bacteria, 100 ml of a culture media containing 0.4% peptone, 0.2% yeast extract, 0.2% 1,3-propanediol, 0.3% $KH_2PO_4$, 0.05% $MgSO_4 \cdot 7H_2O$ (pH 7.0) were added to a shaking flask, and cultured for 40 hours in the same manner as for actinomyces. The bacterial cells were disrupted to obtain a crude enzyme solution.

This crude enzyme solution was mixed with 0.1M Tris-HCl buffer (pH 9.0) containing 0.5 mg/ml INT, 10 mM serinol, 1 mM $NAD^+$ and incubated at 25° C. When $NAD^+$ is reduced into NADH, INT is reduced to form red-purple formazan ($\epsilon$=15000). Based on this reaction, the amino alcohol dehydrogenase activity i n the crude enzyme solution was spectroscopically determined by measuring the change of absorbance at 490 nm. One unit of enzymewas defined as the amount of the enzyme producing 1 $\mu$mol formazan in 1 min under the above condition. Table 1 shows serinol dehydrogenase activity of each strain.

TABLE 1

| Strain | Activity (Unit/100 ml of culture medium) |
| --- | --- |
| Streptomyces virginiae IFO 12827 | 0.85 |
| Streptomyces griseus TPC 33081 | 1.12 |
| Streptomyces avidinii A044 | 0.06 |
| Streptomyces pseudovenezulae A161 | 0.38 |
| Pseudomonas fluorescens B101 | 2.72 |
| Pseudomonas marginalis B102 | 3.20 |
| Burkholdenia cepacia B033 | 1.32 |
| Arthrobacter aurescens B151 | 1.32 |

EXAMPLE 2

Identification of Microorganisms Producing Amino Alcohol Dehydrogenase

Bacteriological characteristics of microorganisms producing amino alcohol dehydrogenase isolated from the soil in Example 1 are as follows.

Strain A044 has sporogenous hyphae in the hock-like or loop-like form, or in the form of untightened coil with a few round (Retinaculum-Apertum(RA)). The color of its aerial hyphae is red, and that of the substrate mycelium is brown. No dispersible pigment is produced. The production of melanin-like pigment is negative in a tyrosine agar medium and is positive in a peptone iron medium. 2,6-Diaminopimelic acid, a cell wall component is LL type, and no mycolic acid is detected. Its 16S rDNA has 99.5% or higher homology with Streptomyces avidinii DSM40526T. Strain A044 was thus confirmed to belong to Streptomyces avidinii species.

Strain A161 has spiral (Spirae) sporogenous hyphae. The color of its aerial hypha is gray, and that of the substrate mycelium is brown. No dispersible pigment is produced. The production of melanin-like pigment is negative in both tyrosine agar medium and peptone iron medium. 2,6-Diaminopimelic acid, a cell wall component is LL type, and no mycoic acid is detected. Its 16S rDNA has 99.5% or higher homology with Streptomyces pseudovenezulae DSM40212T. Strain A161 was thus confirmed to belong to Streptomyces pseudovenezulae species.

Bacteriological characteristics of strain B151 is a gram-positive bacillus (coryneform) with no motility nor sporulation. Both catalase reaction and starch hydrolysis are positive. The type of peptidoglycan of cell walls is A3α, L-Lys-L-Ala-L-Thr-L-Ala. These characteristics indicate that strain B151 belongs to the genus Arthrobacter. Homology between its 16S rDNA and *Arthrobacter aurescens* is 98.8% or higher. Strain A161wa thus confirme[0084] t b[0085] lon to *Arthrobacter aurescens* species.

Bacteriological characteristics of amino alcohol dehydrogenase-producing strains, B101, B102, and B033 are shown in Table 2. Strains B101, B102, and B033 were identified as *Preudomonas fluorescens, Pseudomonas marginalis*, and *Burkholdenia capacia*, respectively.

TABLE 2

| Characteristics | B101 | B 102 | B033 |
|---|---|---|---|
| Cell form | bacillus | bacillus | bacillus |
| Cell size | 0.5–0.8 to 0.8–3.5 μm | 0.5–0.8 to 0.8–3.0 μm | 0.5–0.8 to 1.5–3.0 μm |
| Motility | + | + | – |
| Flagellum | polar flagellum | polar flagellum | none |
| Gram-stain | negative | negative | negative |
| Spore | none | none | none |
| Production of florescent pigment | + | orange | – |
| Catalase | + | + | + |
| Oxidase | + | + | + |
| ADH | + | + | – |
| Nitrate reducing ability | Not tested | Not tested | – |
| Denitrification ability | + | + | – |
| Homology of 16SrRNA | 98% (*P. fluorescens*) | 99.8% (*P. marginalis*) | 99.1% (*B. cepacia*) |

EXAMPLE 3

Cultivation of Microorganisms

*Streptomyces virginiae* IFO 12827 was cultured as follows. One platinum loopful of microbial cells from a slant culture was suspended in 50 ml of a preculture medium (1.0% soluble starch, 0.2% yeast extract, 0.1% meat extract, 0.2% NZ amine, 0.2% malt extract, pH 7.0), inoculated into a sterilized Erlenmeyer flask and shake-cultured at 30° C. for 24 hours under the aerobic condition. Three liters of a main culture medium (1.5% soluble starch, 0.8% soytone, 0.5% meatextract, 0.3% glucose, 0.2% $K_2HPO_4$, 0.3% NaCl, 0.03% $MgSO_4 \cdot 7H_2O$, 0.01% $CaCl_2 \cdot 2H_2O$, 0.1% (v/v) TM solution, and 0.1% (w/v) antiform (Antiform A, Sigma), pH 7.3) was added to a 4-liter jar fermentor and sterilized. The culture broth (50 ml) of the preculture was inoculated therein, and cultured at 30° C. for 48 hours under the aeration conduction at 0.25 vvm/400 rpm.

EXAMPLE 4

Cultivation of Microorganisms

*Streptomyces griseus* TPC 33081, *Streptomyces avidinii* strain A044, and *Streptomyces pseudovenezulae* A161 were cultured in the same manner as in Example 3.

EXAMPLE 5

Cultivation of Microorganisms

One platinum loopful of *Pseudomonas fluorescens* B 101 from a slant culture was added in 50 ml of a preculture medium (0.8% peptone, 0.2% yeast extract, and 0.3% NaCl (pH 7.0)) and inoculated into a sterilized Sakaguchi flask and shake-cultured at 30° C. for 24 hours under the aerobic condition. Three liters of a main culture medium (0.4% peptone, 0.2% yeast extract, 0.2% 1,3-propanediol, 0.3% $K_2HPO_4$, 0.05% $MgSO_4 \cdot 7H_2O$, and 0.1% antiform (Antiform A, Sigma) (pH 7.3)) was added to a 4-liter jar fermentor and sterilized. The culture broth of the preculture was inoculated therein, and cultured at 30° C. for 12 hours under the aeration condition at 0.25 vvm/400 rpm.

EXAMPLE 6

Cultivation of Microorganisms

*Pseudomonas marginalis* B102, *Burkholdenia cepacia* B033, and *Arthrobacter aurescens* strain A161 were culture[0084] in the same manner as in Example 5.

EXAMPLE 7

Purification of Enzymes

Microbial cells were harvested from the liquid culture medium of *Streptomyces virginiae* IFO 12827 by centrifugation to obtain about 230 g of wet microbial cells from 4.5 L of the culture broth. The microbial cells were suspended in 92 ml of 20 mM phosphate buffer (KPB, pH 7.0) containing 0.5 mM phenylmethylsulfonyl fluoride (PMSF). The resulting suspension was treated with a homogenizer for 3 min and ultra-sonicated (20 kHz, 200W) for 20 min for disruption. The disrupted products were centrifuged to obtain supernatant as a crude enzyme solution. Polyethyleneimine (0.01% (w/v)) was added to the crude enzyme solution, stirred, and centrifuged to remove precipitates. The supernatant was dialyzed by ultrafiltration, applied to a Blue-Sepharose column (2.5×24 cm) (Pharmacia) to allow the enzyme to pass through-fraction. This fraction was collected, concentrated by ultrafiltration and allowed to be adsorbed by a serine-Sepharose column (2.5×22 cm) equilibrated with 10 mM KPB (pH 7.0). The enzyme was eluted by the concentration gradient of KPB containing 0 to 1.2 M NaCl and 20 mM serine. The active fraction was collected, concentrated and desalted by ultrafiltration, and allowed to be adsorbed by Gigapite column (5.5 cm×20 cm, Seikagaku Corporation). The enzyme was eluted with 5 to 400 mM KPB (pH 7.0). The active fraction was harvested, concentrated by ultrafiltration, and allowed to be adsorbed by Cellulofine GCL2000sf gel filtration column (1.2×70 cm, Seikagaku Corporation) to elute the enzyme with 10 mM KPB containing 0.1 M NaCl. Thus, 8 units of amino alcohol dehydrogenase were obtained at a yield of 10%.

EXAMPLE 8

Purification of Enzyme

Amino alcohol dehydrogenase was purified from about 100 g of cultured cells of *Pseudomonas fluorescens* B101 in the same manner as in Example 7 except for conducting no treatment with a homogenizer. Sixteen units of amino alcohol dehydrogenase were obtained at a yield of about 6%.

EXAMPLE 9

Enzymatic Properties of the Enzyme

Characteristics of the amino alcohol dehydrogenase derived from *Streptomyces virginiae* IFO 12827 obtained in Example 7 were examined.
1) Molecular Weight The molecular weight of a part of a subunit of the enzyme determined by SDS-polyacrylamide gel electrophoresis was about 46,000 Da, and that of the whole molecule determined by gel filtration was about 100,000 Da.

2) Coenzyme

The enzyme is NAD(H)-dependent and does not use NADP(H) as a coenzyme. It does not exhibit any enzymatic activity in the PMS and 2,6-dichlorophenolindophenol (DCIP) systems, indicating that it does not use PMS as an electron acceptor.

3) Optimum pH

The optimum pH for oxidative deamination reaction using serinol as a substrate is 10.0, and that for reductive amination reaction using dihydroxyacetone is 7.0, as shown in Table 1.

4) Optimum Temperature

The optimum temperature for reductive amination at pH 7.0 is about 30° C.

5) Thermostability

It is relatively stable at 30° C., and inactivated at 40° C. or higher when heated for 30 min at pH 7.0.

6) Substrate Specificity

Table 3 show relative activity to various substrates taking the activity to serinol as 100%. Tables 6 to 8 show relative activity to various substrates when taking the activity to dihydroxyacetone as 100%.

7) Km Values

In reductive amination reaction (pH 7.0, phosphate buffer), Km is 25 mM when $NH_4Cl$ is substrate, 0.022 mM for NADH, and 2.2 mM for dihydroxyacetone. In oxidative deamination reaction (pH 9.0, Tris-HCl buffer), Km is 0.84 mM for $NAD^+$ and 4.0 mM for serinol.

8) Stability

Its activity is stable in the presence of glycerol or serinol, or phenylmethylsulfonylfluoride, a protease inhibitor.

TABLE 3

| Substrate (Amino alcohols) | Relative activity (%) |
|---|---|
| serinol | 100 |
| isoleucinol | 113 |
| L-(−)-methioninol | 85 |
| (S)-(+)-leucinol | 105 |
| DL-2-amino-1-propanol | 214 |
| 2-amino-2-methyl-1-propanol | 115 |
| (+)-2-amino-1-butanol | 109 |
| DL-2-amino-1-pentanol | 103 |
| (S)-(+)-2-amino-3-methyl-1-butanol | 43 |
| (S)-(−)-2-amino-3-phenyl-1-propanol | 120 |
| 2-amino-3-hydroxypyridine | 136 |
| 2-aminocyclohexanol | 113 |

TABLE 4

| Substrate (Amino acids) | Relative activity (%) |
|---|---|
| L-serine | 83 |
| L-alanine | 160 |
| L-aspartic acid | 55 |
| L-glutamic acid | 67 |

TABLE 5

| Substrate (Amines) | Relative activity (%) |
|---|---|
| n-butylamine | 170 |
| n-hexylamine | 173 |
| n-octylamine | 114 |
| benzylamine | 134 |
| (R)-2-aminobutane | 127 |
| 2-aminopentane | 252 |
| 3-aminopentane | 270 |

TABLE 5-continued

| Substrate (Amines) | Relative activity (%) |
|---|---|
| (R)-2-aminoheptane | 91 |
| (R)-1-phenethylamine | 127 |
| 1-methyl-3-phenylpropylamine | 152 |

TABLE 6

| Substrate (Keto alcohols) | Relative activity (%) |
|---|---|
| dihydroxyacetone | 100 |
| hydroxyacetone | 120 |
| 4-hydroxy-2-butanone | 140 |
| 3-hydroxy-2-butanone | 89 |
| 5-hydroxy-2-pentanone | 83 |
| 4-hydroxy-3-hexanone | 94 |
| 5-hydroxy-4-octanone | 83 |
| 2-hydroxyacetophenone | 186 |

TABLE 7

| Substrate (Keto acids) | Relative activity (%) |
|---|---|
| pyrvinic acid | 251 |
| oxalacetic acid | 447 |
| 2-oxoglutaric acid | 107 |

TABLE 8

| Substrate (Ketones/aldehydes) | Relative activity (%) |
|---|---|
| n-butylaldehyde | 117 |
| n-hexylaldehyde | 100 |
| benzaldehyde | 149 |
| acetone | 78 |
| 2-butanone | 267 |
| 2-pentanone | 150 |
| 2-hexanone | 134 |
| acetophenone | 172 |
| 4-phenyl-2-butanone | 134 |

EXAMPLE 10

Enzyme Reaction

1) Conversion of Hydroxyacetone into 2-amino-1-propanol

The amino alcohol dehydrogenase (0.5 unit) obtained in Example 7 was added to 2 ml of a mixture containing 5 mM hydroxyacetone, 10 mM NADH, 0.2M $NH_4Cl$, 0.1 M Tris-HCl buffer (pH 8.0), and the resulting reaction mixture was incubated at 25° C. for 48 hours. The product was analyzed by gas chromatography with a FID detector (column, TENAX TA (3.2 mm×1 m); injection and detection temperature, 25° C.; $N_2$ flow rate, 50 ml/min; column temperature, gradient from 150 to 180° C. (5° C./min); retained at 180° C. for 10 min). As a result, the decrease of hydroxyacetone was detected at the retention time of 2.8 min, and the production of 2-amino-1-propanol was detected at the retention time of 3.7 min. The retention time of 2-amino-1-propanol was completely the same as that of the standard compound. These results revealed that the enzyme converted keto alcohol into amino alcohol.

2) Conversion of Oxalacetic Acid into Aspartic Acid

The same reaction system as used in 1) except for using oxalacetic acid as a substrate in place of hydroxyacetone was incubated at 25° C. for 48 hours. The produced amino acid was converted into an o-phthalaldehyde (OPA) derivative by OPA-derivatization method. The derivative was analyzed by high-performance liquid chromatography (column, CAPCELL PAC C18 AG120 (4.6 mm×25 cm, Shiseido); detection, 340 nm; column temperature, 45° C.; mobile phase flow rate, 1 ml/ min; concentration gradient elution, a) 10 mM sodium phosphate buffer (pH 6.8) to b) acetonitrile:10 mM sodium phosphate buffer (pH 6.8) =2:1). The peak of the product, aspartic acid was observed at the retention time of 6.5 min, which is completely the same as that of the standard compound. These results indicate that the enzyme converts keto acid into amino acid.

3) Conversion of 1-phenethylamine into Acetophenone

The amino alcohol dehydrogenase (0.5 unit) was added to a mixture of 2 mM 1-phenethylamine, 10 mM NAD$^+$ and 0.1, M Tris-HCl buffer (pH 9.0), and the resulting reaction solution was incubated at 25° C. for 48 hours. The reaction solution was adjusted to pH 10.0 with NaOH and extracted with an equivalent volume of ethyl acetate. The product was analyzed by gas chromatography-mass spectrometry (QP-5000GC-MS, Shimadzu, column, DB-1 (0.25 mm×30 m); injection temperature, 180° C.; detection temperature, 250° C.; column temperature, 80° C. retained for 5 min, temperature gradient (10° C./min), then retained for 5 min at 180° C. The retention time for 1-phenethylamine was 5.42 min and that for acetophenone was 5.74 min. The retention time and mass-spectrum of the product were completely the same as those for the standard compound. These results indicate that the enzyme converts amine into ketone.

COMPARISON EXAMPLE 1

L-alanine Dehydrogenase

Known NAD(H)-dependent amino acid dehydrogenases reportedly act on only keto acids and amino acids as substrates (Experiments of Biochemistry, Vol. 11, ed. by Japan Society of Biochemistry, Amino acid metabolism and biological amine (I) 193–218, J. Org. Chem. 55, 5567, 1990; Fermentation and Industry 40, 301–311, 1982). However, it is not reported that the enzymes do not act on amino alcohols at all. Reactivity of a commercially available alanine dehydrogenase to amino alcohols was examined. Reaction was performed at 25° C. for several min in a reaction solution containing 1 mM NAD$^+$, 10 mM of each substrate, 0.1 M Tris-HCl buffer (pH 8.0), and 0.02 unit of alanine dehydrogenase (derived from *Bacillus stearothermophilius*, Seikagaku Corporation). NADH produced was spectroscopically measured at 340 nm. The enzyme acted on L-alanine but not on L-aspartic acid, L-glutamic acid, serinol, DL-2-amino-1-propanol, 1-phenethylamine, (R)-2-aminobutane, nor 2-aminopentane.

COMPARISON EXAMPLE 2

L-glutamate Dehydrogenase

The same experiment as Comparison Example 1 was conducted using L-glutamate dehydrogenase derived from microorganism (Toyobo), and that derived from bovine liver (Lifetech Oriental). Both L-glutamate dehydrogenases acted on L-glutamic acid but not on L-alanine, L-aspartic acid, serinol, DL-2-amino-1-propanol, 1-phenethylamine, (R)-2-aminobutane, nor 2-aminopentane.

What is claimed is:

1. A purified amino alcohol dehydrogenase having the following physicochemical properties:
   (a) NAD(H)-dependent;
   (b) a molecular weight of a part of a subunit of about 46,000 Da when determined by SDS-polyacrylamide gel electrophoresis, and of the whole molecule of about 100,000 Da when determined by gel filtration;
   (c) substrate specificity, such that it acts on amino alcohols, amines, and amino acids in the presence of NAD$^+$ to produce keto alcohols, ketones, aldehydes, and keto acids, and acts on keto alcohols, ketones, aldehydes, and keto acids in the presence of NADH and ammonium ions to produce amino alcohols, amines, and amino acids;
   (d) thermostability, such that it is relatively stable at 30° C. and inactivated at 40° C. or higher when heated at pH 7.0 for 30 min;
   (e) optimum temperature of about 30° C. in reductive amination at pH 7.0;
   (f) optimum pH of 10.0 in oxidative deamination and of 7.0 in reductive animation; and
   (g) stability, such that its activity is stable in the presence of glycerol, serinol, or phenylmethylsulfonylfluoride.

2. The amino alcohol dehydrogenase of claim 1, wherein the amino alcohol dehydrogenase is purified from *Streptomyces virginiae*.

* * * * *